US00PP29063P3

(12) United States Plant Patent
Matsumoto

(10) Patent No.: US PP29,063 P3
(45) Date of Patent: Mar. 6, 2018

(54) *VERBENA* PLANT NAMED 'RIKAV36504'

(50) Latin Name: *Verbena hybrida*
Varietal Denomination: RIKAV36504

(71) Applicant: Rika Matsumoto, Shiga (JP)

(72) Inventor: Rika Matsumoto, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 49 days.

(21) Appl. No.: 14/999,653

(22) Filed: Jun. 9, 2016

(65) Prior Publication Data

US 2017/0359933 P1 Dec. 14, 2017

(51) Int. Cl.
*A01H 5/02* (2006.01)

(52) U.S. Cl.
USPC ..... Plt./308

(58) Field of Classification Search
USPC ..... Plt./308
See application file for complete search history.

*Primary Examiner* — Keith O Robinson
(74) *Attorney, Agent, or Firm* — C. A. Whealy

(57) ABSTRACT

A new and distinct cultivar of *Verbena* plant named 'RIKAV36504', characterized by its compact, mounding and upright to eventually trailing plant habit; moderately vigorous growth habit; freely branching habit; dark green-colored leaves; freely flowering habit; relatively large salmon pink-colored flowers that are held above and beyond the foliar plane; and relative tolerance to Powdery Mildew (*Podosphaera xanthii*).

1 Drawing Sheet

Botanical designation: *Verbena hybrida.*
Cultivar denomination: 'RIKAV36504'.

BACKGROUND OF THE INVENTION

The present invention relates to a new and distinct cultivar of *Verbena* plant, botanically known as *Verbena hybrida*, and hereinafter referred to by the name 'RIKAV36504'.

The new *Verbena* plant is a product of a planned breeding program conducted by the Inventor in Higashiomi, Shiga, Japan and Bonsall, Calif. The objective of the breeding program is to create new vigorous and freely-branching *Verbena* plants with numerous flowers and tolerance to Powdery Mildew (*Podosphaera xanthii*).

The new *Verbena* plant originated from a cross-pollination made by the Inventor on May 20, 2013 in Higashiomi, Shiga, Japan of *Verbena hybrida* 'Lan Peachy', disclosed in U.S. Plant Pat. No. 15,536, as the female, or seed, parent with a proprietary seedling selection of *Verbena hybrida* identified as code number 12V224-02, not patented, as the male, or pollen, parent. The new *Verbena* plant was discovered and selected by the Inventor as a single flowering plant from within the progeny of the stated cross-pollination in a controlled greenhouse environment in Bonsall, Calif. on Jun. 11, 2014.

Asexual reproduction of the new *Verbena* plant by vegetative terminal cuttings in a controlled environment in Bonsall, Calif. has shown that the unique features of this new *Verbena* plant are stable and reproduced true to type in successive generations.

SUMMARY OF THE INVENTION

Plants of the new *Verbena* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'RIKAV36504'. These characteristics in combination distinguish 'RIKAV36504' as a new and distinct *Verbena* plant:

1. Compact, mounding and upright to eventually trailing plant habit.
2. Moderately vigorous growth habit.
3. Freely branching habit.
4. Dark green-colored leaves.
5. Freely flowering habit.
6. Relatively large salmon pink-colored flowers that are held above and beyond the foliar plane.
7. Relatively tolerant to Powdery Mildew (*Podosphaera xanthii*).

Plants of the new *Verbena* can be compared to plants of the female parent, 'Lan Peachy'. Plants of the new *Verbena* differ primarily from plants of 'Lan Peachy' in the following characteristics:

1. Plants of the new *Verbena* have larger flowers than plants of 'Lan Peachy'.
2. Plants of the new *Verbena* and 'Lan Peachy' differ in flower color as plants of 'Lan Peachy' have lighter pink-colored flowers.

Plants of the new *Verbena* can be compared to plants of the male parent selection. Plants of the new *Verbena* differ primarily from plants of the male parent selection in the following characteristics:

1. Plants of the new *Verbena* are more freely branching than plants of the male parent selection.
2. Plants of the new *Verbena* have broader leaves than plants of the male parent selection.

Plants of the new *Verbena* can be compared to plants of the *Verbena hybrida* 'VEAZ0003', disclosed in U.S. Plant Pat. No. 23,596. In side-by-side comparisons, plants of the new *Verbena* differ primarily from plants of 'VEAZ0003' in the following characteristics:

1. Plants of the new *Verbena* are more freely branching than plants of 'VEAZ0003'.
2. Plants of the new *Verbena* have darker green-colored leaves than plants of 'VEAZ0003'.
3. Plants of the new *Verbena* are more tolerant to Powdery Mildew than plants of 'VEAZ0003'.

BRIEF DESCRIPTION OF THE PHOTOGRAPHS

The accompanying colored photographs illustrate the overall appearance of the new *Verbena* plant showing the colors as true as it is reasonably possible to obtain in colored reproductions of this type. Colors in the photographs may differ slightly from the color values cited in the detailed botanical description which accurately describe the actual colors of the new *Verbena* plant.

The photograph at the bottom of the sheet comprises a side perspective view of a typical flowering plant of 'RIKAV36504' grown in a container.

The photograph at the top of the sheet is a close-up view of a typical flowering plant of 'RIKAV36504'.

DETAILED BOTANICAL DESCRIPTION

The aforementioned photographs and following observations and measurements describe plants grown during the spring in 10-cm containers in an acrylic-covered greenhouse in Carleton, Mich. and under cultural practices typical of commercial *Verbena* production. During the production of the plants, day and night temperatures ranged from 18° C. to 30° C. and light levels averaged 1,500 foot-candles. Plants were seven weeks old when the photographs and description were taken. In the following description, color references are made to The Royal Horticultural Society Colour Chart, 2007 Edition, except where general terms of ordinary dictionary significance are used.

Botanical classification: *Verbena hybrida* 'RIKAV36504'.

Parentage:

*Female, or seed, parent.*—*Verbena hybrida* 'Lan Peachy', disclosed in U.S. Plant Pat. No. 15,536.

*Male, or pollen, parent.*—Proprietary seedling selection of *Verbena hybrida* identified as code number 12V224-02, not patented.

Propagation:

*Type cutting.*—Vegetative terminal cuttings.

*Time to initiate roots, summer.*—About three days at temperatures ranging from about 16° C. to 29° C.

*Time to initiate roots, winter.*—About four days at temperatures ranging from about 16° C. to 21° C.

*Time to produce a rooted plant, summer.*—About 15 days at temperatures ranging from about 16° C. to 29° C.

*Time to produce a rooted plant, winter.*—About 20 days at temperatures ranging from about 16° C. to 21° C.

*Root description.*—Medium in thickness, fibrous; white in color.

*Rooting habit.*—Freely branching; medium density.

Plant description:

*Plant and growth habit.*—Compact, mounding and upright to eventually trailing plant habit; freely branching habit with about ten primary lateral branches developing per plant each secondary branches potentially developing at every node; pinching is not required; dense and bushy plant habit; moderately vigorous growth habit.

*Plant height, soil level to top of foliar plane.*—About 9.5 cm.

*Plant height, soil level to top of floral plane.*—About 14 cm.

*Plant diameter (spread).*—About 21.25 cm.

Lateral branch description:

*Length.*—Variable, about 16 cm.

*Diameter.*—About 2 mm.

*Internode length.*—About 2 cm.

*Orientation.*—Initially upright then outwardly spreading to trailing.

*Strength.*—Strong.

*Texture and luster.*—Pubescent; dull.

*Color, developing.*—Close to 146D.

*Color, developed.*—Close to 146A.

Leaf description:

*Arrangement.*—Opposite, simple.

*Length.*—About 2.8 cm.

*Width.*—About 2.4 cm.

*Shape.*—Roughly deltoid.

*Apex.*—Broadly acute to rounded.

*Base.*—Truncate.

*Margin.*—Crenate.

*Texture and luster, upper and lower surfaces.*—Pubescent, coarse, hirsute; dull.

*Venation pattern.*—Pinnate; reticulate.

*Color.*—Developing leaves, upper surface: Close to 146B. Developing leaves, lower surface: Close to 146C. Fully expanded leaves, upper surface: Close to N137A; venation, close to 146A. Fully expanded leaves, lower surface: Close to 146A; venation, close to 146C.

*Petioles.*—Length: About 1 cm. Diameter: About 2 mm. Strength: Moderately strong. Texture and luster, upper and lower surfaces: Pubescent, minute; dull. Color, upper and lower surfaces: Close to 146D.

Flower description:

*Flower arrangement and habit.*—Sessile salverform flowers arranged in upright hemispherical terminal racemes; flowers face upward or outwardly; freely flowering habit with about 28 flowers developing per inflorescence and typically more than 600 flowers developing per plant.

*Natural flowering season.*—Plants flower continuously from spring until frost in Michigan; early flowering habit, plants begin flowering about six weeks after planting.

*Flower longevity.*—Flowers last about four to five days on the plant, flowers not persistent.

*Fragrance.*—None detected.

*Inflorescence height.*—About 3.5 cm.

*Inflorescence diameter.*—About 5.2 cm.

*Flower buds.*—Length: About 1.5 cm. Diameter: About 4 mm. Shape: Elongated oblong. Texture and luster: Smooth, glabrous; matte. Color: Close to 34B.

*Flower diameter.*—About 1.7 cm by 1.9 cm.

*Flower depth (height).*—About 2.4 cm.

*Throat diameter.*—About 1.5 mm.

*Tube length.*—About 2 cm.

*Tube diameter, distally.*—About 1.5 mm.

*Corolla.*—Arrangement: Single whorl of five fused petals fused towards the base into a narrow tube.

Petal lobe length: About 9 mm. Petal lobe width: About 9 mm. Petal lobe shape: Roughly cordate. Petal lobe apex: Emarginate. Petal margin: Entire; with development, reflexing; moderately undulate. Petal texture and luster, upper surface: Smooth, glabrous; dull. Petal texture and luster, lower surface: Mostly smooth and glabrous with minute hairs near the tube; dull. Throat texture: Mostly smooth and glabrous, distally with minute hairs; dull. Tube texture: Pubescent, minute; slightly glossy. Color: Petal, when opening, upper surface: Close to 42A to 42B. Petal, when opening, lower surface: Close to 42D. Petal, fully opened, upper surface: Close to 33C; venation, close to 33C; color becoming closer to 49B to 49C with development. Petal, fully opened, lower surface: Close to 31D; venation, close to 31D; color becoming closer to 49D with development. Throat: Close to 145D; venation, close to 145D. Tube: Close to 145C to 145D; venation, close to 145C to 145D.

*Calyx*.—Arrangement: Single whorl of five fused sepals fused towards the base into a slender tube. Sepal length: About 9 mm. Sepal width: Less than 1 mm. Sepal shape: Narrowly lanceolate. Sepal apex: Acute. Sepal margin: Entire. Sepal texture and luster, inner surface: Smooth, glabrous; slightly glossy. Sepal texture and luster, outer surface: Pubescent; minute; dull. Sepal color, upper surface: Close to 145B. Sepal color, lower surface: Close to 146A.

*Peduncles*.—Length: About 3.8 cm. Diameter: About 2 mm. Strength: Strong. Aspect: Upright to about 45° from vertical. Texture and luster: Pubescent; dull. Color: Close to 146A.

*Reproductive organs*.—Stamens: Quantity and arrangement: Four per flower, filaments partially adnate to corolla tube. Filament length: About 1.2 cm. Filament color: Close to 145D. Anther shape: Round. Anther size: About 1 mm by 1 mm. Anther color: Close to 151A. Pollen amount: Scarce. Pollen color: Close to 151D. Pistils: Quantity: One per flower. Pistil length: About 2 cm. Stigma shape: Rounded, bi-parted. Stigma diameter: About 1 mm. Stigma color: Close to 144A. Style length: About 1.7 cm. Style color: Close to 145B. Ovary color: Close to 145B. Fruits and seeds: Fruit and seed development have not been observed on plants of the new *Verbena*.

Temperature tolerance: Plants of the new *Verbena* have been observed to tolerate temperatures from about 2° C. to about 40° C. and are suitable for USDA Hardiness Zones 8 to 11.

Pathogen & pest resistance: Plants of the new *Verbena* have been observed to be relatively tolerant to Powdery Mildew (*Podosphaera xanthii*). Plants of the new *Verbena* have not been observed to be resistant to pests and other pathogens common to *Verbena* plants.

It is claimed:

1. A new and distinct *Verbena* plant named 'RIKAV36504' as illustrated and described.

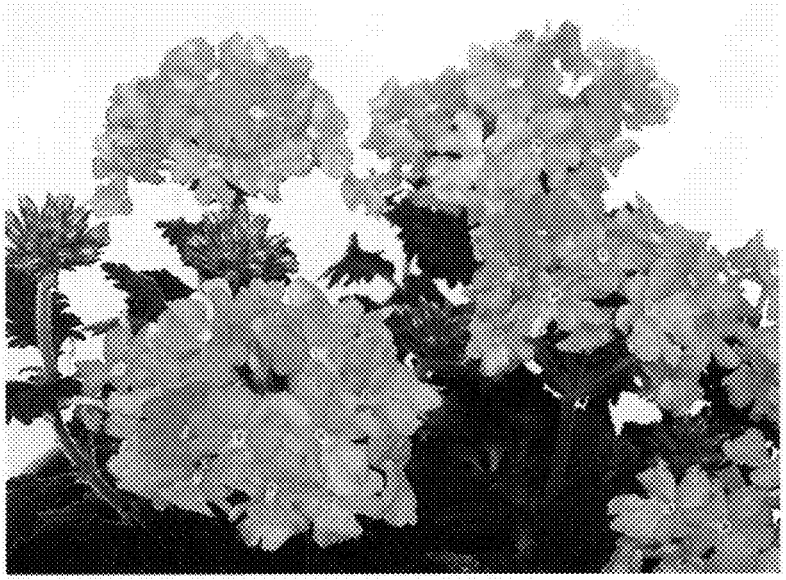
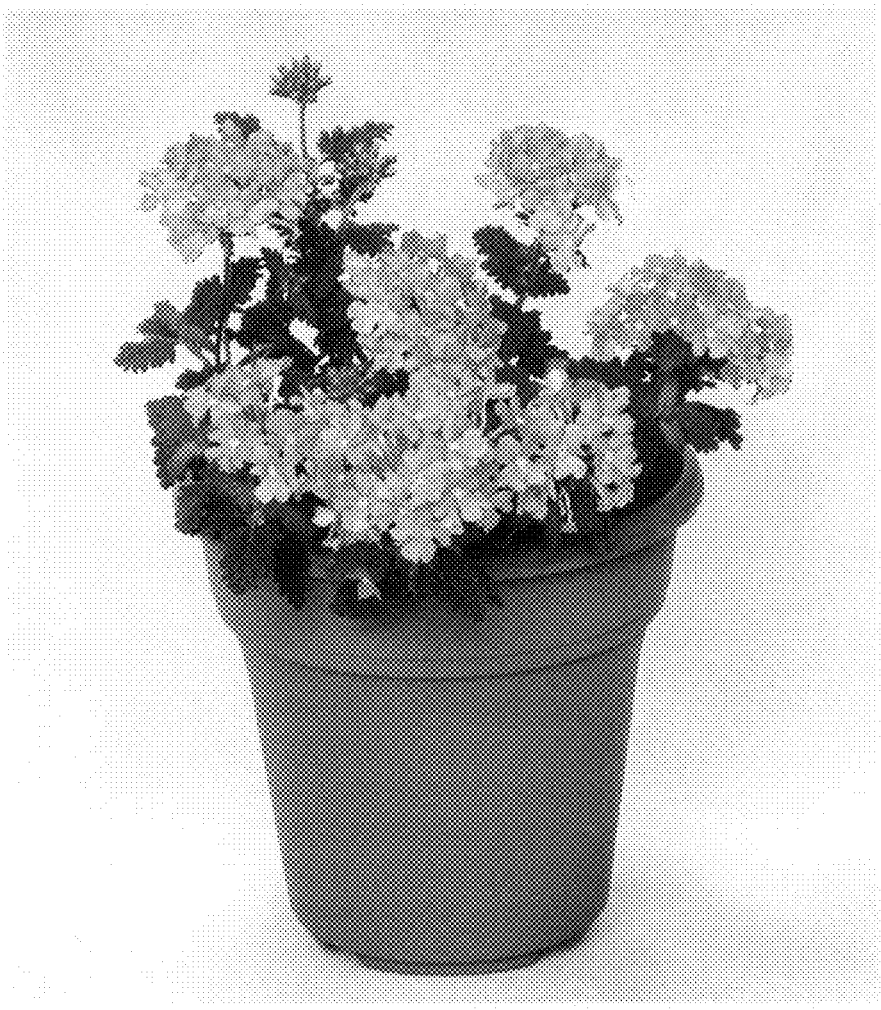

* * * * *